United States Patent

Shimizu et al.

[11] Patent Number: 5,238,827
[45] Date of Patent: Aug. 24, 1993

[54] PROCESS FOR PREPARING GLYCINE FROM GLYCINONITRILE

[75] Inventors: Hitoshi Shimizu; Chiharu Fujita; Takakazu Endo; Ichiro Watanabe, all of Kanagawa, Japan

[73] Assignee: Nitto Chemical Industry Co., Ltd., Tokyo, Japan

[21] Appl. No.: 677,176

[22] Filed: Mar. 29, 1991

[30] Foreign Application Priority Data

Mar. 30, 1990 [JP] Japan ................................. 2-80696

[51] Int. Cl.$^5$ .......................... C12P 13/04; C12N 1/12
[52] U.S. Cl. ................................ 435/106; 435/252.1
[58] Field of Search ............................ 435/106, 252.1

[56] References Cited

U.S. PATENT DOCUMENTS 3,940,316  2/1976  Commeyras et al. ............... 435/106

FOREIGN PATENT DOCUMENTS 0187680  1/1986  European Pat. Off. .

OTHER PUBLICATIONS

Patent Abstract of Japan, C field, vol. 11, No. 132, Apr. 24, 1987.

*Primary Examiner*—David M. Naff
*Assistant Examiner*—Michael V. Meller
*Attorney, Agent, or Firm*—Sughrue, Mion, Zinn, Macpeak & Seas

[57] ABSTRACT

A process for preparing glycine from glycinonitrile by reacting glycinonitrile with a hydrolase produced by a microorganism, wherein the microorganism is a member of a genus selected from the group consisting of Rhodococcus, Arthrobacter, Caseobacter, Pseudomonas, Enterobacter, Acinetobacter, Alcaliqenes, and Streptomyces. The process involves no by-production, and the microorganism has high hydrolizing activity to convert glycinonitrile to glycine.

8 Claims, No Drawings

PROCESS FOR PREPARING GLYCINE FROM GLYCINONITRILE

FIELD OF THE INVENTION

This invention relates to a process for preparing glycine from glycinonitrile using microorganisms. Glycine is of importance as a food additive or a starting material for synthesizing pharmaceuticals and agricultural chemicals.

BACKGROUND OF THE INVENTION

A conventional process for preparing glycine on an industrial scale comprises synthesizing glycinonitrile by a Stretcker's synthesis using prussic acid, formaldehyde and ammonia as main starting materials and hydrolyzing the resulting glycinonitrile with a caustic alkali. This process has significant disadvantages, such as coloring of the reaction mixture, unsuitable side reactions that form by-products, e.g., iminodiacetic acid, etc., and the necessity of removal and disposal of a large quantity of by-produced salts. Such disadvantages result in increased cost and production time due to additional purification processes required for decoloration and removal of by-products.

Alternatively, glycine can be prepared by biological hydrolysis of glycinonitrile using microorganisms belonging to the genus Brevibacterium or Corynebacterium, as disclosed e.g., in JP-B-58-15120 (corresponding to U.S. Pat. No. 3,940,316) and JP-A-61-162191 (corresponding to European Patent Publication No. 0187680A) (the terms "JP-B" and "JP-A" as used herein mean an "examined published Japanese patent application" and an "unexamined published Japanese patent application", respectively). However, known biological processes for glycine production suffer from the problem of low enzymatic activity and provide only low concentrations of accumulated glycine, while also requiring the use of large quantities of microbial cells, and hence are not well suited for practical commercial applications.

SUMMARY OF THE INVENTION

Accordingly, an object of the present invention is to provide methods for preparing glycine using microorganisms, which produce no by-products and which have industrial advantages from the viewpoint of both energy consumption and yield.

The inventors have discovered a microorganisms which exhibit a high activity of producing metabolic enzymes that hydrolyze glycinonitrile and which additionally lack an activity for decomposing or assimilating the produced glycine. Such microorganisms have also been discovered to be suitable for commercial production of glycine. As a result, the inventors have discovered that microorganisms belonging to the genera Rhodococcus, Arthrobacter, Caseobacter, Pseudomonas, Enterobacter, Acinetobacter, Alcaligenes, and Streptomyces are highly efficient and suitable for producing glycine from glycinonitrile according to methods of the present invention, such as for commercial production of glycine using conventional techniques.

These and other objects of the present invention can be achieved by providing a process for preparing glycine from glycinonitrile comprising reacting said glycinonitrile with a hydrolase produced by one or more microorganisms, wherein said microorganisms belong to the genus Rhodococcus, Arthrobacter, Caseobacter, Pseudomonas, Enterobacter, Acinetobacter, Alcaligenes, or Streptomyces and are capable of hydrolyzing glycinonitrile.

DETAILED DESCRIPTION OF THE INVENTION

Specific examples of glycine-producing strains belonging to the above-mentioned genera include Rhodococcus sp. SK49 (FERM P-11303), Rhodococcus sp. SK70 (FERM P-11304), Rhodococcus sp. SK92 (FERM BP-3324), Rhodococcus sp. HR11 (FERM P-11306), Arthrobacter sp. SK103 (FERM P-11300), Arthrobacter sp. HR1 (FERM BP-3323), Arthrobacter sp. HR4 (FERM P-11302), Caseobacter sp. BC4 (FERM BP-3316), Pseudomonas sp. SK10 (FERM P-11307), Pseudomonas sp. SK11 (FERM P-11308), Pseudomonas sp. SK13 (FERM BP-3325], Pseudomonas sp. SK31 (FERM P-11310), Pseudomonas sp. SK87 (FERM P-11311), Enterobacter sp. SK12 (FERM BP-3322), Acinetobacter sp. BC9-2 (FERM BP-3317), Alcaligenes sp. BC16-2 (FERM BP-3321), and Streptomyces griseus (IFO 3355), and variants of these strains.

Of these microorganisms, Streptomyces griseus (IFO 3355) is known strain that is readily available from The Institute for Fermentation, Osaka (IFO) under the deposit number described above.

The above-mentioned strains except Streptomyces griseus (IFO 3355) are new strains isolated from soils by the present inventors and have been deposited with Fermentation Research institute, Agency of Industrial Science & Technology under the deposit numbers (FERM P Nos. or FERM BP Nos.) listed above. The morphological and physiological properties of these new strains are described below.

| SK49 and SK70 | | |
|---|---|---|
| | SK49 | SK70 |
| Growth condition in meat extract-agar slant medium | satisfactory growth, rough surface with no luster, pink | satisfactory growth, rough surface with luster, pink |
| Shape | polymorphic bacillus | polymorphic bacillus |
| Gram staining | + | + |
| Spore | − | − |
| Mobility | − | − |
| Oxidase | − | − |
| Catalase | + | + |
| Rod-coccus cycle | − | − |
| Extension of periphery of colony | not observed | not observed |
| Growth under anaerobic conditions | − | − |
| Diamino acid of cell wall | meso-diamino-pimelic acid | meso-diamino-pimelic acid |
| Glycolyl test | + (glycolyl type) | + (glycolyl type) |
| Sugar composition of cell wall: | | |
| Arabinose | + | + |
| Galactose | + | + |
| Existence of Quinone | MK-8 (H$_2$) | MK-8 (H$_2$) |

| SK92 and HR11 | | |
|---|---|---|
| | SK92 | HR11 |
| Growth condition in meat extract-agar slant medium | satisfactory growth, smooth surface with luster, pink | satisfactory growth, smooth surface with luster, white |
| Shape | polymorphic bacillus | polymorphic bacillus |

-continued

| | | |
|---|---|---|
| Gram staining | + | + |
| Spore | − | − |
| Mobility | − | − |
| Oxidase | − | − |
| Catalase | + | + |
| Rod-coccus cycle | − | − |
| Extension of periphery of colony | not observed | not observed |
| Growth under anaerobic conditions | − | − |
| Diamino acid of cell wall | meso-diamino-pimelic acid | meso-diamino-pimelic acid |
| Glycolyl test | + (glycolyl type) | + (glycolyl type) |
| Sugar composition of cell wall: | | |
| Arabinose | + | + |
| Galactose | + | + |
| Existence of Quinone | MK-8 ($H_2$) | MK-8 ($H_2$) |

SK103 and HR1

| | SK103 | HR1 |
|---|---|---|
| Growth condition in meat extract-agar slant medium | moderate growth, smooth surface with luster, semi-transparent, white | satisfactory growth, smooth surface with luster, semi-transparent, white |
| Shape | polymorphic bacillus | polymorphic bacillus |
| Gram staining | + | + |
| Spore | − | − |
| Mobility | − | − |
| Oxidase | − | − |
| Catalase | + | + |
| Rod-coccus cycle | + | + |
| Extension of periphery of colony | not observed | not observed |
| Growth under anaerobic conditions | − | − |
| Diamino acid of cell wall | lysine | lysine |
| Glycolyl test | − (acetyl type) | − (acetyl type) |
| Sugar composition of cell wall: | | |
| Arabinose | − | − |
| Galactose | − | − |
| Existence of Quinone | MK-9 ($H_2$) | MK-9 ($H_2$) |

HR4 and BC4

| | HR4 | BC4 |
|---|---|---|
| Growth condition in meat extract-agar slant medium | satisfactory growth, smooth surface with luster, semi-transparent, white | satisfactory growth, rough surface with no luster, orange |
| Shape | polymorphic bacillus | polymorphic bacillus |
| Gram staining | + | + |
| Spore | − | − |
| Mobility | − | − |
| Oxidase | − | − |
| Catalase | + | + |
| Rod-coccus cycle | + | + |
| Extension of periphery of colony | not observed | not observed |
| Growth under anaerobic conditions | − | − |
| Diamino acid of cell wall | lysine | meso-diamino-pimelic acid |
| Glycolyl test | − (acetyl type) | − (acetyl type) |
| Sugar composition of cell wall: | | |
| Arabinose | − | + |
| Galactose | − | + |
| Existence of Quinone | MK-9 ($H_2$) | MK-9 ($H_2$) |

SK10 and SK11

| | SK10 | SK11 |
|---|---|---|
| Growth condition in meat extract-agar slant medium | poor growth, rough surface with luster, semi-transparent, pale brownish white | poor growth, rough surface with luster, semi-transparent, pale yellowish white |
| Shape | bacillus | bacillus |
| Gram staining | − | − |
| Spore | − | − |
| Mobility | + | + |
| Flagella | polar | polar |
| Oxidase | + | + |
| Catalase | + | + |
| O-F test | O | O |

SK13 and SK31

| | SK13 | SK31 |
|---|---|---|
| Growth condition in meat extract-agar slant medium | poor growth, rough surface with luster, semi-transparent, pale yellowish white | poor growth, rough surface with luster, semi-transparent, white |
| Shape | bacillus | bacillus |
| Gram staining | − | − |
| Spore | − | − |
| Mobility | + | + |
| Flagella | polar | polar |
| Oxidase | + | + |
| Catalase | + | + |
| O-F test | O | O |

SK87

| | |
|---|---|
| Growth condition in meat extract-agar slant medium | moderate growth, rough surface with luster, semi-transparent, pale brownish white |
| Shape | bacillus |
| Gram staining | − |
| Spore | − |
| Mobility | + |
| Flagella | polar |
| Oxidase | + |
| Catalase | + |
| O-F test | O |

SK12

| | |
|---|---|
| Shape | bacillus |
| Gram staining | − |
| Spore | − |
| Mobility | + |
| Oxidase | − |
| Catalase | + |
| O-F test | F |
| Production of gas from glucose | − |
| Indole production | − |
| Methyl Red | + |
| VP test | − |
| Utilization of citric acid | + |
| Hydrogen sulfide production | − |
| Decomposition of urea | − |
| Deamination reaction of phenylalanine | + |
| Decarboxylation reaction of lysine | − |
| Arginine dihydrolase | − |
| Decarboxylation reaction of ornithine | − |

BC9-2 and BC16-2

| | BC9-2 | BC16-2 |
|---|---|---|
| Shape | bacillus | bacillus |
| Gram staining | − | − |

| -continued | | |
|---|---|---|
| Spore | — | — |
| Mobility | — | + |
| Flagella | NT | peritrichous |
| Oxidase | — | + |
| Catalase | + | + |
| O-F test | — | alkalization |
| 3-Ketolactose production | NT | — |
| Existence of Quinone | NT | Q-8 |

NT: Not tested.

The above-described taxonomical properties were examined by referring to *Bergey's Manual of Systematic Bacteriology* (1986) and, as a result, SK49, SK70, SK92, and HR11 strains were identified to belong to the genus Rhodococcus; SK103, HR1 and HR4 strains to the genus Arthrobacter: BC4 strain to the genus Caseobacter; SK10, SK11, SK13, SK31, and SK87 to the genus Pseudomonas; SK12 to the genus Enterobacter; BC9-2 to the genus Acinetobacter; and BC16-2 to the genus Alcaligenes, respectively.

Culture media which can be used for culturing microorganisms according to the present invention can contain enzyme inducers, such as nitrile compounds and amide compounds, known assimilable carbon sources and nitrogen sources, and inorganic nutrients necessary for growth according to known methods. Culturing is preferably aerobically conducted under controlled pH and temperature conditions, e.g. at a pH of about 4 to 10 and a temperature of about 20° to 50° C.

The hydrolysis reaction is carried out by suspending (i) culture or microbial cells recovered therefrom; (ii) treated microbial cells (cell extracts or purified enzyme); or (iii) immobilized microbial cells or enzyme; in water, a buffer solution or physiological saline, followed by adding thereto glycinonitrile to prepare an aqueous solution containing about 0.01 to 10% by weight of the microbial cells, cell extracts or purified enzyme, on a dry basis, and about 0.1 to 20% by weight of glycinonitrile, and allowing the mixture to react at a temperature of about the freezing point to 60° C., and preferably about 10° to 40° C., at a pH of about 5 to 11, and preferably about 6 to 10, for a period of about 0.5 to 50 hours.

Thus, glycinonitrile is converted to glycine and ammonia at a molar yield up to about 100%, which glycine and ammonia are accumulated in the form of a glycine ammonium salt in a high concentration. Glycine is then separated from the glycine ammonium-containing reaction solution by known techniques, such as concentration, ion exchange, extraction, and crystallization.

The present invention is characterized by using microorganisms capable of hydrolyzing glycinonitrile to produce and accumulate glycine with high reaction activity, at high selectivity of glycine and in an extremely high concentration. The present invention thus provides an industrially satisfactory process for preparing glycine.

The present invention is now illustrated in greater detail with reference to the following Examples, but it should be understood that the present invention is not deemed to be limited thereto.

EXAMPLE 1

(1) Culturing:

Each of the microorganisms shown in Table 1 below was inoculated to a plate medium having the following composition and cultured at 30° C. for 3 days.

| Medium Composition | |
|---|---|
| Glycerol | 5 g/l |
| 2-Chloropropionitrile | 0.5 ml/l |
| Yeast extract | 0.2 g/l |
| $K_2HPO_4$ | 3 g/l |
| $Na_2SO_4$ | 0.3 g/l |
| $MgCl_2$ | 0.2 g/l |
| $CaCl_2$ | 40 mg/l |
| $MnSO_4.4H_2O$ | 4 mg/l |
| $FeCl_3.7H_2O$ | 0.7 mg/l |
| $ZnSO_4$ | 0.1 mg/l |
| Agar | 18 g/l |
| pH | 7.2 |

(2) hydrolysis of Glycinonitrile:

A given amount of the microbial cells was taken out of each plate and washed with a 0.05 M phosphate buffer solution (pH=7.7). the cells collected by centrifugation were suspended in 1 ml of the same phosphate buffer solution, and a 0.5 ml aliquot thereof was added to 0.5 ml of a 0.05 M phosphate buffer solution(pH=7.7) containing 200 mM glycinonitrile, followed by allowing the system to react at 30° C. for 48 hours. After completion of the reaction, the system was subjected to centrifugation to remove the microbial cells. The supernatant liquor was analyzed by HPLC to determine glycine produced. The results obtained are shown in Table 1.

TABLE 1

| Microorganism | Glycine Produced* |
|---|---|
| Rhodococcus sp. SK49 | ++ |
| Rhodococcus sp. SK70 | +++ |
| Rhodococcus sp. SK92 | +++ |
| Rhodococcus sp. HR11 | +++ |
| Arthrobacter sp. SK103 | + |
| Arthrobacter sp. HR1 | ++ |
| Arthrobacter sp. HR4 | + |
| Caseobacter sp. BC4 | ++ |
| Pseudomonas sp. SK10 | +++ |
| Pseudomonas sp. SK11 | ++ |
| Pseudomonas sp. SK13 | +++ |
| Pseudomonas sp. SK31 | + |
| Pseudomonas sp. SK87 | +++ |
| Enterobacter sp. SK12 | + |
| Acinetobacter sp. BC9-2 | + |
| Alcaligenes sp. BC16-2 | + |
| Streptomyces griseus (IFO 3355) | ++ |

Note:
+:  0.1 to 0.5 g/l
++:  0.5 to 1.0 g/l
+++:  1.0 to 3.0 g/l

EXAMPLE 2

(1) Culturing:

Rhodococcus sp. SK92 was cultured in a medium having the following composition at 30° C. for 3 days.

| Medium Composition | |
|---|---|
| Propionitrile | 10 ml/l |
| Glucose | 10 g/l |
| Yeast extract | 5 g/l |
| $MgSO_4.7H_2O$ | 0.5 g/l |
| $KH_2PO_4$ | 0.8 g/l |
| $K_2HPO_4$ | 2.5 g/l |
| pH | 7.5 |

(2) Hydrolysis of Glycinonitrile:

The microbial cells were collected from the culture by centrifugation, washed with a 0.05 M phosphate buffer solution (pH=7.7), and suspended in the same buffer solution in a concentration of 0.8% by weight on a dry basis. To 60 ml of the resulting cell suspension was added 1.7 g of glycinonitrile, and the system was allowed to react at 40° C. while controlling the pH between 7.9 and 8.1. Glycinonitrile was hydrolyzed nearly completely in 6 hours to produce glycine at a molar yield of approximately 100%. At this point, 1.7 g of glycinonitrile was further added to continue the reaction. In 13 hours from the start of the reaction, 90 g/l of glycine was produced. At this point, as the reaction appeared to further proceed, 3.4 g of glycinonitrile was furthermore added to the reaction system to continue the reaction. As a result, 148 g/l of glycine was produced and accumulated in an overall reaction time of 30 hours. The yield of glycine was found to be almost 100% with no by-production of glycine amide.

EXAMPLE 3

Microbial cells were collected by centrifugation from a culture of Rhodococcus sp. SK92 obtained in the same manner as in Example 2 and washed with a 0.05 M phosphate buffer solution (pH=7.7). A 0.05 M phosphate buffer solution (pH=8.0) containing 0.8% by weight (on dry basis) of the thus prepared active microbial cells and 12.0% by weight of glycinonitrile was prepared and allowed to react at 40° C. for 42 hours while controlling the pH between 7.9 and 8.1. As a result, 168 g/l of glycine was produced and accumulated. Substantially no unreacted glycinonitrile or glycine amide as a by-product was detected, indicating that the reaction had proceeded almost quantitatively and completely.

While the invention has been described in detail and with reference to specific examples thereof, it will be apparent to one skilled in the art that various changes and modifications can be made therein without departing from the spirit and scope thereof.

What is claimed is:

1. A process for preparing glycine from glycinonitrile comprising reacting said glycinonitrile with a hydrolase produced by a microorganism, wherein said microorganism is a member of a genus selected from the group consisting of Rhodococcus, Arthrobacter, Caseobacter, Pseudomonas, Enterobacter, Acinetobacter, Alcaligenes, and Streptomyces.

2. The process as claimed in claim 1, wherein said microorganism is selected from the group consisting of Rhodococcus sp. SK49 (FERM P-11303), Rhodococcus sp. SK70 (FERM P-11304), Rhodococcus sp. SK92 (FERM Bp 3324), Rhodococcus sp. HR11 (FERM P-11306), Arthrobacter sp. SK103 (FERM P-11300), Arthrobacter sp. HR1 (FERM BP-3323), Arthrobacter sp. HR4 (FERM P-11302), Caseobacter sp. BC4 (FERM BP-3316), Pseudomonas sp. SK10 (FERM P-11307), Pseudomonas sp. SK11 (FERM P-11308), Pseudomonas sp. SK13 (FERM BP-3325), Pseudomonas sp. SK31 (FERM P-11310), Pseudomonas sp. SK87 (FERM P-11311), Enterobacter sp. SK12 (FERM BP-3322), Acinetobacter sp. BC9-2 (FERM BP-3317), Alcaligenes sp. BC16-2 (FERM BP-3321), and Streptomyces griseus (IFO 3355).

3. The process according to claim 1, wherein a molar yield of said glycine is about 100% relative to the amount of said glycinonitrile reacted with said hydrolase.

4. The process according to claim 1, wherein the reaction of said glycinonitrile with said hydrolase produces a reaction product substantially in the form of glycine ammonium salt.

5. The process according to claim 1, wherein said process is carried out in an aqueous solution comprising, as dry weight, about 0.1 to 20% of said glycinonitrile and further comprising, as dry weight, about 0.1 to 10% of said hydrolase.

6. The process according to claim 1, wherein said glycinonitrile is admixed with at least one of said microorganisms which produce said hydrolase.

7. The process according to claim 1, wherein said glycinonitrile is admixed with cell extract of at least one of said microorganisms which produce said hydrolase.

8. The process according to claim 1, wherein said hydrolase is present as purified enzyme.

* * * * *